United States Patent [19]

Satoh et al.

[11] Patent Number: 5,034,543

[45] Date of Patent: Jul. 23, 1991

[54] ASCORBIC ACID DERIVATIVE AND USE AS ANTIOXIDANTS

[75] Inventors: Toshio Satoh; Yasunori Niiro; Hisao Kakegawa; Hitoshi Matsumoto, all of Tokushima, Japan

[73] Assignee: Nippon Hypox Laboratories Incorporated, Tokyo, Japan

[21] Appl. No.: 382,269

[22] Filed: Jul. 20, 1989

[51] Int. Cl.$^5$ .................. C07D 307/32; C09K 15/22
[52] U.S. Cl. .................. 549/315; 252/403; 252/407
[58] Field of Search ........................ 549/315

[56] References Cited

U.S. PATENT DOCUMENTS 4,780,549 10/1988 Tenao et al. .................. 549/315

OTHER PUBLICATIONS

Cabral et al., Chem. Abstracts, vol. 109, 25, 231442f (1988).

Primary Examiner—Johann Richter
Attorney, Agent, or Firm—Nixon & Vanderhye

[57] ABSTRACT

This invention relates to a novel ascorbic acid derivative having excellent antioxidant action, particularly eliminating action on superoxides and a process for preparing the same. Furthermore, this invention also relates to a novel antioxidant comprising the afore-mentioned novel ascorbic acid derivative or other known ascorbic acid derivatives.

3 Claims, No Drawings

ASCORBIC ACID DERIVATIVE AND USE AS ANTIOXIDANTS

BACKGROUND OF THE INVENTION (1) Field of the Invention

This invention relates to an ascorbic acid derivative, a process for preparing the same and an antioxidant comprising an ascorbic acid derivative.

(2) Prior Art

Ascorbic acid has antioxidant action and is used for the purpose of preventing browning of foods, retaining flavor or freshness of foods or the like.

Ascorbic acid, however, is susceptible to decomposition and sometimes hard to produce the above-mentioned effects over a long period.

SUMMARY OF THE INVENTION

It is, therefore, a first object of this invention to provide a novel ascorbic acid derivative eliminating the aforementioned disadvantages of the ascorbic acid. It is a second object of this invention to provide a process for preparing the aforesaid novel ascorbic acid derivative. It is further a third object of this invention to provide an antioxidant comprising an ascorbic acid derivative.

The first object of this invention has been achieved by an ascorbic acid derivative represented by the general formula (Ia):

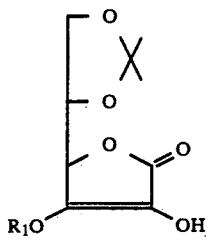

(Ia)

wherein $R_1$ is a group selected from the group consisting of a heterocyclic ring-containing alkyl group, an alkylcarbonylalkyl group and an arylcarbonylalkyl group.

The second object of this invention has been accomplished by a process for preparing an ascorbic acid derivative represented by the general formula (Ia):

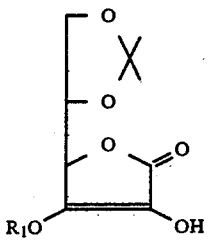

(Ia)

wherein $R_1$ is a group selected from the group consisting of a heterocyclic ring-containing alkyl group, an alkylcarbonylalkyl group and an arylcarbonylalkyl group, comprising reacting 5,6-O-isopropylidene ascorbic acid represented by the formula (II):

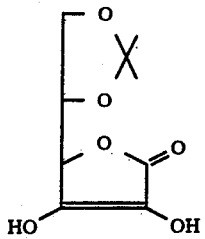

(II)

with an organic halide selected from the group consisting of a heterocyclic ring-containing alkyl halide, an alkylcarbonylalkyl halide and an arylcarbonylalkyl halide.

Furthermore, the third object of this invention has been achieved by an antioxidant comprising an ascorbic acid derivative represented by the general formula (IA):

(IA)

wherein $R_2$ is a group selected from the group consisting of an alkyl group, a heterocyclic ring-containing alkyl group, an aralkyl group, a hydroxycarbonylalkyl group, an alkoxycarbonylalkyl group, an aralkoxycarbonylalkyl group, an alkenyl group, a hydroxyalkyl group, an alkoxyalkyl group, an alkylcarbonylalkyl group, an arylcarbonylalkyl group and a cyanoalkyl group.

The group $R_1$ in the general formula (Ia) representing the novel ascorbic acid derivative of this invention is different in the number of substituent groups defined therein from the group $R_2$ in the general formula (IA) representing the ascorbic acid derivative constituting the antioxidant of this invention. Although the group $R_1$ has three substituent groups, the group $R_2$ has the total 12 substituent groups including the three. This means that ascorbic acid derivatives which are not novel can also be used as the antioxidant of this invention.

DETAILED DESCRIPTION OF THE INVENTION

The novel ascorbic acid derivative of this invention is initially explained hereinafter.

The novel ascorbic acid derivative of this invention is represented by the general formula (Ia):

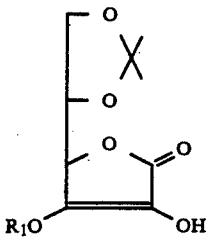

(Ia)

wherein R₁ is a group selected from the group consisting of a heterocyclic ring-containing alkyl group, an alkylcarbonylalkyl group and an arylcarbonylalkyl group.

Heterocyclic ring-containing alkyl groups having 1 to 3 nitrogen atoms in the ring are herein preferred as the heterocyclic ring-containing alkyl groups, and examples thereof include groups represented by the general formulae:

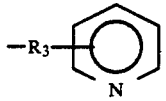

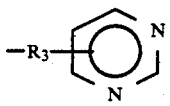

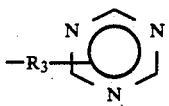

wherein $R_3$ is an alkylene group which may optionally have a branched chain. Particularly preferred heterocyclic ring-containing alkyl groups are pyridylmethyl group, pyrimidylmethyl group, triazylmethyl group and the like.

Examples of the alkylcarbonylalkyl groups include groups represented by the general formula:

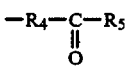

wherein $R_4$ is an alkylene group which may optionally have a branched chain; $R_5$ is an alkyl group which may optionally have a branched chain. Particularly preferred alkylcarbonylalkyl groups are

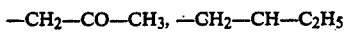

and the like.

Furthermore, examples of the arylcarbonylalkyl groups include groups represented by the general formula:

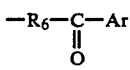

wherein $R_6$ is an alkylene group which may optionally have a branched chain; Ar is an aryl group which may optionally have a substituent group on the ring. Particularly preferred arylcarbonylalkyl groups are —CH₂—CO—C₆H₅ and the the like.

The novel ascorbic acid derivative of this invention has excellent antioxidant action and can be preferably used as food antioxidants or beautifying and whitening cosmetics.

The novel ascorbic acid derivative of this invention is an extremely specific compound in that it has the ability to eliminate superoxides having the possibility of damaging biomolecules and tissues, and application as a medicine is also considered for treating diseases derived from such superoxides.

The process for preparing the novel ascorbic acid derivative represented by the above-mentioned general formula (Ia) of this invention is explained hereinafter.

In the process of this invention, 5,6-O-isopropylidene ascorbic acid represented by the formula (II):

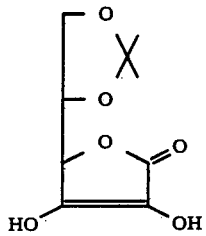

(II)

is used as a starting material.

Such a compound represented by the formula (II) is obtained by ketalizing ascorbic acid according to a conventional method.

In the process of this invention, the compound represented by the general formula (II) is reacted with an organic halide selected from the group consisting of a heterocyclic ring-containing alkyl halide, an alkylcarbonylalkyl halide and an arylcarbonylalkyl halide to etherify the hydroxyl group at the 3-position of the compound represented by the general formula (II) and thereby provide the desired compound represented by the general formula (Ia). The dehydrohalogenation may be carried out according to a method wherein the compound represented by the general formula (II) is mixed under stirring with an organic halide in an organic solvent such as DMF, DMSO, THF, hexamethylphosphoramide or the like. It may be conducted by vigorously stirring the compound represented by the general formula (II) and an organic halide in the presence of a quaternary ammonium salt-phase transfer catalyst such as tetrabutylammonium bromide, N-acetonylpridinium bromide, allyltriethylammonium bromide, N-aminopyridinium iodide or the like, in a reaction system comprising an organic solvent phase (a non-aqueous solvent, such as methyl ethyl ketone, benzene, methylene chloride, chloroform or the like) and an aqueous phase (water). The above-mentioned organic solvent such as DMF, DMSO, THF, hexamethylphosphoramide or the like may be used as the organic solvent, depending on the kind of the aforesaid phase transfer catalyst.

The former method is suitable for using alkylcarbonylalkyl halides or arylcarbonylalkyl halides as the organic halide, and the latter method is suitable for using the above-mentioned two kinds of organic halides and also for using heterocyclic ring-containing alkyl halides.

The antioxidant of this invention is explained hereinafter.

As explained above, the antioxidant of this invention comprises the ascorbic acid derivative represented by the general formula (IA):

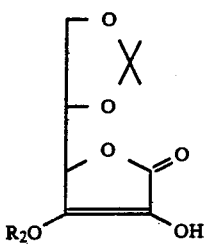

(IA)

The group $R_2$ in the formula is within a wider scope than the group $R_1$ in the general formula (Ia) representing the novel ascorbic acid derivative as described above, and therefore the ascorbic acid derivative represented by the general formula (IA) includes also known compounds.

Thus, the group $R_2$ includes the same three substituent groups (heterocyclic ring-containing alkyl group, alkylcarbonylalkyl group and arylcarbonylalkyl group) as the group $R_1$, besides those, further nine substituent groups of an alkyl group, an aralkyl group, a hydroxycarbonylalkyl group, an alkoxycarbonylalkyl group, an aralkoxycarbonylalkyl group, an alkenyl group, a hydroxyalkyl group, an alkoxyalkyl group and a cyanoalkyl group. The term "alkyl" in the aforesaid substituent groups means a straight or branched alkyl group. The term "alkoxy" means an alkoxy group consisting of a straight or branched alkyl group and oxygen. The term "alkenyl" means a straight or branched alkenyl group having at least one unsaturated double bond.

Such an ascorbic acid derivative represented by the general formula (IA) has a radical eliminating ability and is preferably used as an antioxidant. The ascorbic acid derivative wherein $R_2$ is an alkylcarbonylalkyl group is extremely desirable, since it has the ability to eliminate superoxides. The ascorbic acid derivative of this invention is also excellent in stability with time.

EXAMPLES

Examples of this invention are illustrated hereinafter.

EXAMPLE 1

Preparation of novel ascorbic acid derivative (Ia) ($R_1$ is alkylcarbonylalkyl)

(1) Synthesis of L-5,6-0-isopropylideneascorbic acid which is a starting material Ascorbic acid in an amount of 180 g was stirred in 750 ml of acetone and warmed to 40° C. Acetyl chloride in a volume of 20 ml was added, and stirring was continued to form a slurry layer.

After 3 hours, the slurry layer was cooled with ice to collect deposited precipitates by filtration. The resulting precipitates were washed with a mixture of cold acetone-n-hexane (3:7) on a funnel and dried with silica gel under reduced pressure.

Recrystallization from acetone was then carried out to provide 190 g of L-5,6-O-isopropylidene-ascorbic acid (melting point: 206°–208° C.).

(2) Synthesis of L-5,6-O-isopropylidene-3-O-(3-butanone)ascorbic acid

In 30 ml of dimethyl sulfoxide (DMSO), was dissolved 4.32 g of the compound obtained in (1). Sodium hydrogencarbonate in an amount of 1.66 g was added, and the resulting solution was stirred. After 30 minutes, 4 g of 2-butanone bromide was added, and the obtained solution was warmed to 50° C. After warming the solution for 20 hours, distilled water (100 ml) and ethyl acetate (100 ml×2) were added to shake the reaction solution. Organic layers were combined, washed with water, shaken with saturated sodium chloride solution and dried over sodium sulfate. An oily substance obtained by concentrating under reduced pressure was subjected to silica gel chromatography and eluted with benzene-ethyl acetate to provide L-5,6-O-isopropylidene-3-O-(3-butanone) ascorbic acid (corresponding to compound No. 022 in Table-1 mentioned below) which was an oily substance. The resulting compound No. 022 of this invention was subjected to antioxidant tests described below.

Furthermore, the method in (2) of Example 1 could be applied to preparation of L-5,6-isopropylidene-3-O-(propanone) ascorbic acid (corresponding to compound No. 021 in Table-1 mentioned below).

EXAMPLE 2

Preparation of novel ascorbic acid derivative (Ia) ($R_1$ is alkylcarbonylalkyl)

The L-5,6-O-isopropylideneascorbic acid obtained in (1) of Example 1 was used as a starting material to carry out the reaction of the above-mentioned starting material with an organic halide in the presence of a phase transfer catalyst in the reaction system consisting of an organic phase and aqueous phase. Details of the reaction are as follows. Thus, 4.15 g of sodium hydrogencarbonate was dissolved in 100 ml of distilled water, and 200 ml of methyl ethyl ketone and 10.80 g of the aforementioned starting material were added. To the resulting mixture solution, 9.25 g of chloroacetone as an organic halide and 0.80 g of tetrabutylammonium bromide as a phase transfer catalyst were added. The obtained mixture was heated to 60° C. and vigorously stirred. After 16 hours, the aqueous layer was adjusted to pH 4 to 5 with 4N hyrochloric acid to separate and collect the organic layer. The aqueous layer was shaken with 200 ml of ethyl acetate, and the resulting organic layer was combined with the aforesaid organic layer, washed with water and then dried over sodium sulfate. Isopropyl ether and petroleum ether were successively added to an oily substance obtained under reduced pressure to collect deposited precipitates by filtration. The obtained precipitates were recrystallized from ethyl acetate saturated with water to afford L-5,6-O-isopropylidene-3-O-methylcarbomethylascorbic acid (corresponding to compound No. 021 in Table-1 mentioned below) having the melting point of 71° C. The resulting compound No. 021 of this invention was used for the antioxidant tests described below.

EXAMPLE 3

Preparation of novel ascorbic acid derivative (Ia) ($R_1$ is 2'-pyridylmethyl)

The procedures similar to those in Example 1 were carried out, except that 2'-pyridylmethyl bromide was used as an organic halide in place of chloroacetone and various reaction conditions were modified according to change of the organic halide to obtain L-5,6-O-isopropylidene-3-O-2'-pyridylmethylascorbic acid (corresponding to compound No. 007 in Table-1 mentioned below) having the melting point of 144° to 145° C. The compound No. 007 of this invention was used for the antioxidant test mentioned below.

REFERENTIAL EXAMPLE 1

Preparation of other ascorbic acid derivatives included in the ascorbic acid derivative (IA)

The L-5,6-O-isopropylideneascorbic acid obtained in (1) of Example 1 was used as a starting material, and reaction was carried out according to the method described in (2) of Example 1 to provide 22 ascorbic acid derviatives designated as compound Nos. 001, 002, 003, 004, 005, 006, 008, 009, 010, 011, 012, 013, 014, 015, 016, 017, 018, 019, 020, 023, 024 and 025 in Table-1 mentioned below. The resulting ascorbic acid derivatives were used for the antioxidant tests described below.

The compound Nos. 003 an 006 could be synthesized by the method mentioned in Example 2.

TABLE 1

| Compound No. | $R_1$ | mp | NMR δ value |
|---|---|---|---|
| 001 | $-(CH_2)_{17}CH_3$ | 41.5–43° C. | 0.88 (3H, m) 1.29 (32H, 6Hm) 4.15 (3H, m) 4.49 (2H, t) 4.67 (H, d, 3Hz) |
| 002 | $-(CH_2)_{11}CH_3$ | Oily substance | 0.88 (3H, m) 1.30 (20H, 6Hm) 4.15 (3H, m) 4.49 (2H, t) 4.67 (H, d, 3Hz) |
| 003 | $-(CH_2)_7CH_3$ | Oily substance | 0.89 (3H, m) 1.29 (12H, 6Hm) 4.15 (3H, m) 4.49 (2H, t) 4.67 (H, d, 3Hz) |
| 004 | $-(CH_2)_3CH_3$ | Oily substance | 0.94 (3H, m) 1.29 (4Hm) 1.34 (3H, s), 1.35 (3H, s) 4.15 (3H, m) 4.48 (2H, t) 4.67 (H, d, 3Hz) |
| 005 | $-CH(CH_3)-CH_2CH_3$ | Oily substance | 0.97 (3H, t) 1.30 (6Hs) 1.37 (3H, d) 1.65 (2H, m) 4.16 (3H, m) 4.65 (H, d, d) 4.95 (H, m) |
| 006 | $-CH_2-C_6H_5$ 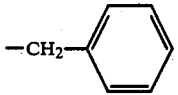 | 105–106° C. | 1.30 (6H, s) 4.15 (3H, m) 4.66 (H, d, 3Hz) 5.49 (2H, s) 7.37 (5H, bs) |
| 007 | $-CH_2-(2\text{-pyridyl})$ 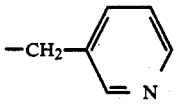 | 144–145° C. | 1.29 (6H, s) 4.14 (3H, m) 4.72 (H, d, 3Hz) 5.59 (2H, s) 7.47 (H, m) 7.97 (H, m) 8.53 (H, m) 8.63 (H, m) |
| 008 | $-(CH_2)_4COOC_2H_5$ | Oily substance | 1.21 (3H, t) 1.29 (6H, s) 1.77 (2H, m) 2.37 (2H, m) 4.09 (2H, q) 4.16 (3H, m) 4.51 (2H, m) 4.69 (H, d, 3Hz) |
| 009 | $-(CH_2)_{16}COOH$ | Oily substance | 1.30 (16H, m) 1.37 (3H, s) 1.40 (3H, s) 2.36 (2H, t) 4.15 (3H, m) 4.49 (2H, t) 4.57 (H, d, 3Hz) |
| 010 | $-(CH_2)_3COOC_2H_5$ | Oily substance | 1.22 (3H, t) 1.29 (6H, s) 2.17 (2H, m) 2.47 (2H, m) 4.10 (2H, q) 4.15 (3H, m) 4.53 (2H, t) 4.70 (H, d, 3Hz) |
| 011 | $-CH_2CH=CH_2$ | Oily substance | 1.29 (6H, s) 4.15 (3H, m) 4.71 (H, d, 3Hz) 4.98 (2H, m) 5.28 (H, m) 5.43 (H, m) 6.10 (H, m) |
| 012 | $-CH_2CH_2OH$ | Oily substance | 1.30 (6H, s) 3.83 (2H, t) 4.15 (3H, m) 4.52 (2H, t, H, s) 4.68 (H, d, 3Hz) |
| 013 | $-CH_2OCH_3$ | 92° C. | 1.29 (6H, s) 3.51 (3H, s) 4.15 (3H, m) 4.77 (H, d, 3Hz) 5.46 (2H, s) |
| 014 | $-CH(CH_3)-COOC_2H_5$ | Oily substance | 1.26 (3H, d, t) 1.30 (6H, s) 1.55 (3H, dd) 4.15 (5H, m) 4.75 (H, d, 3Hz) 5.40 (H, m) |
| 015 | $-CH_2COOH$ | Oily substance | 1.31 (6H, s) 4.15 (3H, m) 4.76 (H, d, 3Hz) 5.05 (2H, d, 2Hz) |
| 016 | $-CH_2COOCH_2-C_6H_5$ 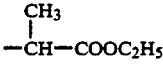 | Oily substance | 1.29 (3H, s) 1.30 (3H, s) 4.15 (3H, m) 4.75 (H, d, 3Hz) 5.11 (2H, s) 5.25 (2H, s) 7.36 (5H, s) |
| 017 | $-CH_2COOC(CH_3)_3$ | 116–122° C. | 1.29 (3H, s) 1.44 (9H, s) 4.15 (3H, m) 4.70 (H, d, 3Hz) 4.84 (2H, s) |
| 018 | $-CH_2COO\text{-n-}C_{10}H_{21}$ | 52–54° C. | 0.88 (3H, m) 1.30 (6H, 16H, m) 4.16 (5H, m) 4.74 (H, d, 3Hz) 5.03 (2H, s) |
| 019 | $-CH_2COOC_4H_9$ | Oily substance | 0.91 (3H, m) 1.31 (6H, s) 1.56 (4H, m) 4.14 (5H, m) 4.76 (H, d, 3Hz) 5.04 (2H, s) |
| 020 | $-CH_2COOC_2H_5$ | 94° C. | 1.26 (3H, t) 1.31 (6H, s) 4.14 (5H, m) |

TABLE 1-continued

| Compound No. | R₁ | mp | NMR δ value |
|---|---|---|---|
| 021 | —CH₂COOCH₃ | 71° C. | 4.76 (H, d, 3Hz) 5.03 (2H, s) 1.27 (6H, s) 2.09 (3H, s) 4.16 (3H, m) |
| 022 | —CH₂COC₂H₅ | Oily substance | 4.86 (H, d, 3Hz) 5.03 (2H, s) 1.04 (3H, t) 1.31 (6H, s) 2.55 (2H, q) 4.15 (3H, m) 4.77 (H, d, s) 5.10 (2H, s) |
| 023 | —CH₂CO—⟨phenyl⟩ | 175° C. | 1.33 (6H, s) 4.20 (3H, m) 4.84 (H, d, 4Hz) 5.85 (2H, d, 2Hz) 7.62 (3H, m) 8.01 (2H, m) |
| 024 | —CH₂CN | Oily substance | 1.29 (6H, s) 4.14 (3H, m) 4.84 (H, d, 3Hz) 5.36 (2H, s) |
| 025 | —CH₂CH₃ | 105° C. | 1.28 (6H, s) 1.34 (3H, t) 4.12 (3H, m) 4.51 (2H, q) 4.65 (H, d, 3Hz) |

TEST EXAMPLE 1

(Antioxidant action examined by using stable radicals)

Reduction activity of α,α-diphenyl-β-picrylhydrazyl (DPPH) which was a stable free radical was examined according to the M. S. Blois method (Nature, vol. 181, page. 1199, 1958) and used as an index to antioxidant action. Thus, specimens were added to 3 ml of a 0.1 mM DPPH solution in ethanol, and absorbance at a wavelength of 517 nm was measured using a spectrophotometer after 20 minutes. The difference in absorbance from the solvent control [0.5% or less of dimethylformamide (DMF)] was taken as the reduction activity.

The 50% radical eliminating concentrations for the test compounds are shown in Table-2.

As can be seen from Table-2, the tested compounds of this invention were found to have improved antioxidant action.

TABLE-2

| Compound No. | 50% radical eliminating concentration |
|---|---|
| 001 | $3.0 \times 10^{-5}$ M |
| 002 | 2.9 |
| 003 | 2.7 |
| 004 | 2.5 |
| 005 | 3.2 |
| 006 | 2.2 |
| 007 | 2.3 |
| 008 | 1.6 |
| 009 | 2.5 |
| 010 | 1.6 |
| 011 | 3.3 |
| 012 | 3.5 |
| 013 | 1.7 |
| 014 | 2.6 |
| 015 | 3.1 |
| 016 | 2.5 |
| 017 | 2.5 |
| 018 | 2.8 |
| 019 | 2.5 |
| 020 | 2.3 |
| 021 | 1.7 |
| 022 | 2.0 |
| 023 | 2.4 |
| 024 | 3.1 |
| 025 | 2.2 |

TEST EXAMPLE 2

(Effects on formazan formation in the xanthine-xanthine oxidase-Nitrotetrazolium Blue system)

Specimens were added to a 0.05M phosphate buffer solution (pH 7.8) containing xanthine, EDTA 2Na and Nitrotetrazolium Blue (NTB) so as to provide the respective final concentrations of $5 \times 10^{-5}$ M, $1 \times 10^{-4}$ M and $5 \times 10^{-4}$ M and warmed at 30° C. for 3 minutes. Xanthine oxidase (manufactured by Sigma Corp.) was added, and the resulting specimens were warmed at 30° C. for 10 minutes to colorimetrically determine formazan formed by superoxide anion radicals. The inhibition ratio of formazan formation was determined from the results at concentrations of 0.5 mM and 4 mM of each specimen.

Results are shown in Table-3. As can be seen from Table-3, tested compound Nos. 021 and 022 of this invention remarkably inhibited formazan formation and therefore the compound of this invention has excellent ability to eliminate superoxide anion radicals.

TABLE-3

| Compound | Concentration (mM) | Inhibition ratio (%) of formazan formation |
|---|---|---|
| 021 | 0.5 | 9.2 |
|  | 4 | 47.4 |
| 022 | 0.5 | 22.6 |
|  | 4 | 26.7 |

As detailed above, this invention provides a novel ascorbic acid derivative having excellent antioxidant action, particularly eliminating action on superoxides and a process for preparing the same.

Furthermore, this invention also provides a novel antioxidant comprising the afore-mentioned novel ascorbic acid derivative or other known ascorbic acid derivatives.

What is claimed is:

1. An ascorbic acid derivative represented by the formula (Ia):

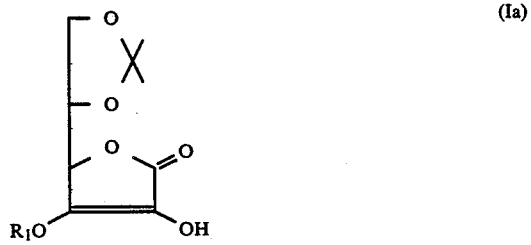

(Ia)

wherein R₁ is selected from the group consisting of an alkylcarbonylalkyl group and an arylcarbonylalkyl group; said alkylcarbonylalkyl group being represented by the formula:

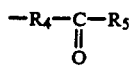

wherein $R_4$ represents an akylene group which may optionally have a branched chain and $R_5$ represents an alkyl group which may optionally have a branched chain, and said arylcarbonylaklyl group being represented by the formula:

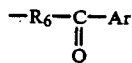

wherein $R_6$ represents an alkylene group which may optionally have a branched chain and Ar is a aryl group.

2. An ascorbic acid derivative of claim 1, wherein said alkylcarbonylalkyl group is selected from the group consisting of $-CH_2-CO-CH_3$ and $-CH_2-CO-C_2H_5$.

3. An ascorbic acid derivative of claim 1, wherein said arylcarbonylalkyl group is $-CH_2-CO-C_6H_5$.

* * * * *